US009525886B2

(12) United States Patent
Lee

(10) Patent No.: US 9,525,886 B2
(45) Date of Patent: Dec. 20, 2016

(54) METHOD FOR IMAGE COMPRESSION AND PRE-DIAGNOSIS IN THREE-DIMENSIONAL REMOTE ULTRASOUND DIAGNOSTIC APPARATUS

(71) Applicant: KOREA DIGITAL HOSPITAL EXPORT AGENCY, Seoul (KR)

(72) Inventor: Min Hwa Lee, Seoul (KR)

(73) Assignee: KOREA DIGITAL HOSPITAL EXPORT AGENCY, Seoul (KR)

( * ) Notice: Subject to any disclaimer, the term of this patent is extended or adjusted under 35 U.S.C. 154(b) by 121 days.

(21) Appl. No.: 14/423,710

(22) PCT Filed: Aug. 30, 2013

(86) PCT No.: PCT/KR2013/007799
§ 371 (c)(1),
(2) Date: Jul. 29, 2015

(87) PCT Pub. No.: WO2014/035175
PCT Pub. Date: Mar. 6, 2014

(65) Prior Publication Data
US 2015/0326872 A1 Nov. 12, 2015

(30) Foreign Application Priority Data
Aug. 31, 2012 (KR) ........................ 10-2012-0096345

(51) Int. Cl.
*H04N 19/48* (2014.01)
*G06T 7/00* (2006.01)
(Continued)

(52) U.S. Cl.
CPC ............. *H04N 19/48* (2014.11); *A61B 8/5215* (2013.01); *A61B 8/565* (2013.01); *G06T 7/0012* (2013.01);
(Continued)

(58) Field of Classification Search
CPC ... A61B 5/1128; A61B 1/00009; A61B 6/032; A61B 5/0033; A61B 6/5217; A61B 6/5211; A61B 6/5205; G06K 2209/051; G06T 9/005; H04N 1/413; H04N 1/4135; H04N 1/415; H04N 1/417; H04N 1/4172; H04N 1/4175; H04N 1/4177; H04N 1/419
See application file for complete search history.

(56) References Cited

U.S. PATENT DOCUMENTS

2007/0010743 A1   1/2007   Arai

FOREIGN PATENT DOCUMENTS

JP   4300488 B2   7/2009
JP   4621338 B2   1/2011
(Continued)

OTHER PUBLICATIONS

International Search Report for PCT/KR2013/007799 mailed Dec. 26, 2013 from Korean Intellectual Property Office.

*Primary Examiner* — Duy M Dang
(74) *Attorney, Agent, or Firm* — Revolution IP, PLLC

(57) ABSTRACT

A method of compressing and pre-diagnosing an image in a three-dimensional remote ultrasound diagnostic apparatus, the method including: a first step of combining two-dimensional images scanned by a scanning unit and generating a three-dimensional volume image, by a processing unit; a second step of selecting a compression scheme for the three-dimensional volume image and compressing the three-dimensional volume image using the selected compression scheme; a third step of storing the compressed three-dimensional volume image in a database unit; a fourth step of pre-diagnosing an abnormal three-dimensional volume image from among stored three-dimensional volume images; and a fifth step of transmitting the abnormal three-
(Continued)

dimensional volume image to a hospital capable of providing a diagnosis, by a data transmitting unit.

22 Claims, 3 Drawing Sheets

(51) Int. Cl.
*G06T 9/00* (2006.01)
*A61B 8/08* (2006.01)
*A61B 8/00* (2006.01)

(52) U.S. Cl.
CPC ........... *G06T 7/0014* (2013.01); *G06T 7/0081* (2013.01); *G06T 9/00* (2013.01); *A61B 8/483* (2013.01); *A61B 8/52* (2013.01); *A61B 8/56* (2013.01); *G06T 2207/10132* (2013.01)

(56) References Cited

FOREIGN PATENT DOCUMENTS

| | | |
|---|---|---|
| JP | 4891651 B2 | 3/2012 |
| KR | 10-2007-0054329 A | 5/2007 |

(A)  (B)

METHOD FOR IMAGE COMPRESSION AND PRE-DIAGNOSIS IN THREE-DIMENSIONAL REMOTE ULTRASOUND DIAGNOSTIC APPARATUS

CROSS REFERENCE TO PRIOR APPLICATIONS

This application is a National Stage Application of PCT International Patent Application No. PCT/KR2013/007799 filed on Aug. 30, 2013, under 35 U.S.C. §371, which claims priority to Korean Patent Application No. 10-2012-009634 filed on Aug. 31, 2012, which are all hereby incorporated by reference in their entirety.

TECHNICAL FIELD

The present invention relates to compressing, diagnosing, and pre-diagnosing an image in a three-dimensional remote ultrasound diagnostic apparatus, and more particularly, to a method of providing a pre-diagnosis by performing a lossy or lossless compression in accordance with the communication circumstances of a data transmitting unit in a three-dimensional remote ultrasound diagnostic apparatus capable of a remote diagnosis and analyzing data features.

BACKGROUND ART

In general, an ultrasonic image diagnostic apparatus, which emits an ultrasonic wave to a human body, detects a reflection wave returned from the human body, performs appropriate signal processing, and displays the processing result on a screen, has been widely used in a medical field since an image of an internal organ may be observed in real time without needing to make an incision in the body.

The ultrasonic image diagnostic apparatus tends to switch from analog to digital and switch from a two-dimensional ultrasound diagnostic apparatus to a three-dimensional or four-dimensional ultrasound diagnostic apparatus, and provides a stereoscopic image as a real-time video and facilitates remote diagnosis from a remote place through a volume image network.

However, for the remote diagnosis, three-dimensional data obtained through a field examination is transmitted to a large hospital or a hospital having a medical team who can diagnose an ultrasonic image. In this case, when a communication environment is bad, it takes much time to transmit the three-dimensional data.

DISCLOSURE

Technical Problem

The present invention is directed to performing lossy compression or lossless compression in accordance with the communication circumstances of a data transmission unit, allowing a three-dimensional volume image to be transmitted to a screening place in a short time.

The present invention is also directed to analyzing features of a compressed and stored three-dimensional volume image to perform a pre-diagnosis on the image.

Technical Solution

One aspect of the present invention provides a method including a first step of a processing unit combining two-dimensional images scanned by a scanning unit to generate a three-dimensional volume image, a second step of selecting a compression scheme for the three-dimensional volume image and compressing the three-dimensional volume image using the selected compression scheme, a third step of storing the compressed three-dimensional volume image in a database unit, a fourth step of pre-diagnosing an abnormal three-dimensional volume image from among stored three-dimensional volume images, and a fifth step of a data transmitting unit transmitting the abnormal three-dimensional volume image to a hospital capable of providing a diagnosis.

Another aspect of the present invention provides a three-dimensional remote ultrasound diagnostic apparatus including a scanning unit configured to generate two-dimensional volume images of an inside of a human body using an ultrasonic signal, a processing unit configured to combine the two-dimensional volume images acquired through the scanning unit to generate a three-dimensional volume image and then compress and pre-diagnose the three-dimensional volume image in units of a specific part or organ, and a database unit configured to store the compressed three-dimensional volume image.

Advantageous Effects

Accordingly, the method of compressing and pre-diagnosing an image in a three-dimensional remote ultrasound diagnostic apparatus according to the present invention has an effect of quickly transmitting a three-dimensional volume image to a diagnosing hospital by performing the lossy or lossless compression on the three-dimensional volume image.

The present invention also has another effect of providing a pre-diagnosis by analyzing a size of the compressed three-dimensional volume image and using a statistical similarity verification algorithm.

MODES OF THE INVENTION

The terms or words used in the specification and claims should not be construed as being limited to typical or dictionary meanings, but construed as the meaning and concept corresponding to the technical idea of the present invention on the basis of the principle that an inventor can appropriately define the concept of the term for describing his or her invention in the best method.

Accordingly, the configurations illustrated in embodiments and drawings described in the specification do not represent the technical idea of the present invention but are just exemplary embodiments. Thus, it should be understood that various equivalents and modifications may exist which can replace at the time of application of this specification.

Hereinafter, exemplary embodiments of the present invention will be described in detail with reference to the accompanying drawings.

Figure 1:
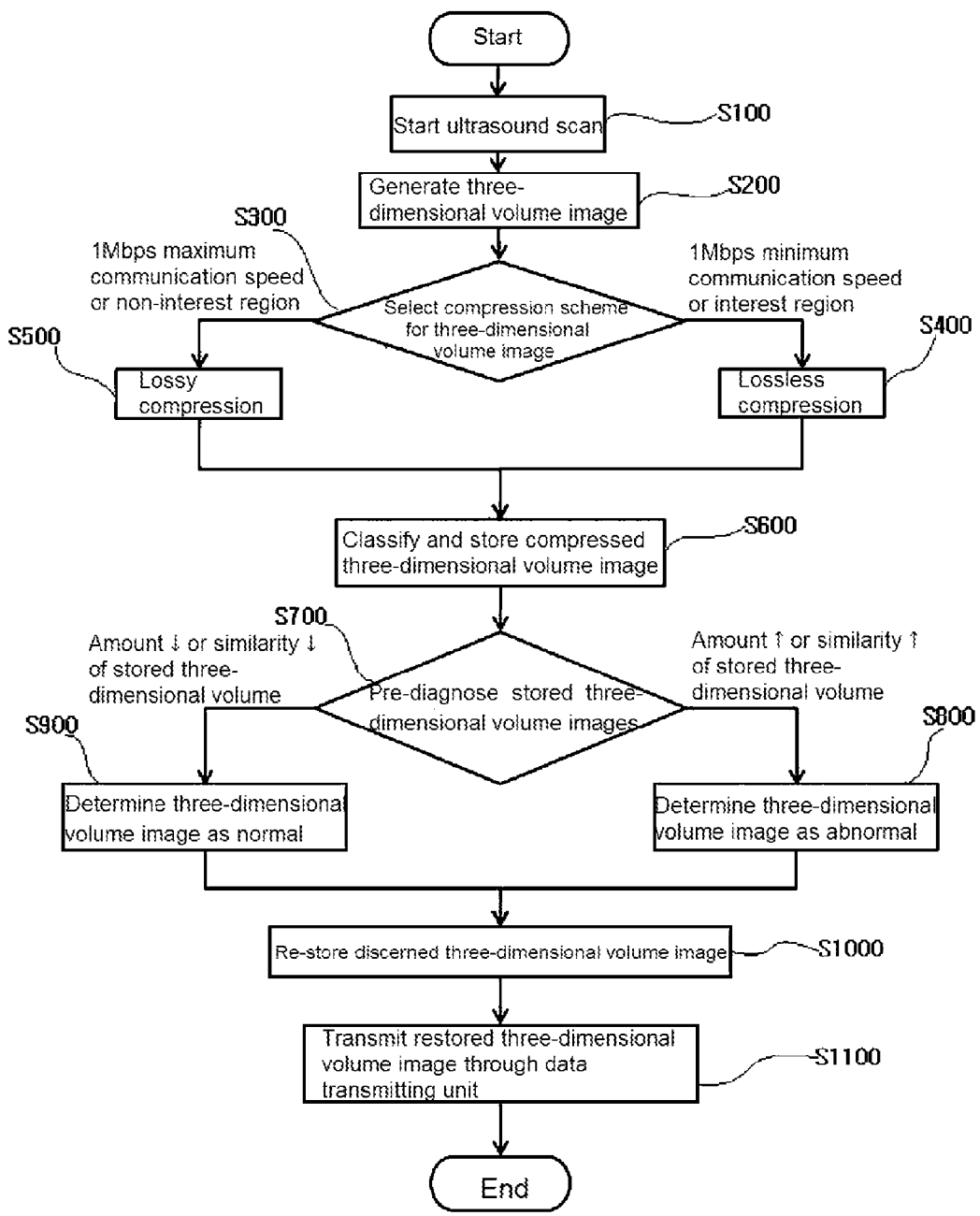
FIG. 1 is a flowchart showing a method of compressing and pre-diagnosing an image of a three-dimensional remote ultrasound diagnostic apparatus according to the present invention.

FIG. 1 is a flowchart showing a method of compressing and pre-diagnosing an image of a three-dimensional remote ultrasound diagnostic apparatus according to the present invention. The method includes a first step of combining two-dimensional images scanned by a scanning unit to generate a three-dimensional volume image, by a processing unit, a second step of selecting a compression scheme for the three-dimensional volume image and compressing the three-dimensional volume image using the selected compression scheme, a third step of storing the compressed three-dimensional volume image in a database unit, a fourth step of pre-diagnosing an abnormal three-dimensional volume image from among the stored three-dimensional volume images, and a fifth step of a data transmitting unit transmitting the abnormal three-dimensional volume image to a hospital capable of providing a diagnosis.

A sonographer starts an ultrasound scan using a scanning unit 100 (S100), and a processing unit 200 combines scanned images to generate a three-dimensional volume image (S200). The processing unit 200 determines whether to perform a lossy compression or lossless compression on the three-dimensional volume image (S300). A compression scheme is selected using one or more of a ping rate, a degree of packet loss, and a data transfer rate as a communication rate of a data transmitting unit 500. Specifically, the lossy compression is performed when the communication rate is less than 1 Mbps, and the lossless compression is performed when the communication rate is equal to or more than 1 Mbps.

The three-dimensional volume image is divided into an area of interest and an area of no interest according to similarity of feature values such as brightness, color, texture, and movement, using an image segmentation technique. The lossless compression is performed on the area of interest (S400), and the lossy compression is performed on the area of no interest (S500). The area of interest may be found by using a watershed algorithm which is an example of an image segmentation technique or analyzing a change in the gradient of the volume image.

For the lossless compression, one or more of ZIP and RAR are used. Alternatively, another lossless compression scheme may be used to compress images. For the lossy compression, one or more of a wavelet algorithm and a movement compensation algorithm are used. Alternatively, another lossy compression scheme may be used.

The lossy or lossless compressed three-dimensional volume image is classified according to race, blood type, height, weight, disease name, and the like, using a data mining technique and then stored in a database unit 300 (S600). In the data mining technique, three-dimensional volume images are classified and stored according to the attribute information of the patients, and the classified and stored three-dimensional volume images are established as an image group. In addition, a standard three-dimensional volume image is generated by applying a statistical technique to the patient data accumulated in the established image group, and then utilized to pre-diagnose the generated three-dimensional volume image.

The compressed three-dimensional volume image is pre-diagnosed such that the compressed three-dimensional volume image may be efficiently transmitted to a hospital capable of providing a diagnosis (S700). An abnormal three-dimensional volume image and a normal three-dimensional volume image are distinguished through the pre-diagnosis. The method includes comparing sizes between a compressed and stored three-dimensional volume image and a normal standard three-dimensional volume image stored in the database unit 300, and determining the compressed and stored three-dimensional volume image as the abnormal three-dimensional volume image when the size of the compressed and stored three-dimensional volume image is greater (S800) and determining the compressed and stored three-dimensional volume image as the normal three-dimensional volume image when the size is equal to that of the normal standard three-dimensional volume image (S900). With a statistical similarity verification algorithm, the compressed and stored three-dimensional volume image is determined as the abnormal three-dimensional volume image when a similarity between the three-dimensional volume image and an abnormal standard three-dimensional volume image stored in the database unit 300 is high (S800) and determined as the normal three-dimensional volume image when the similarity is low (S900).

The determined three-dimensional volume image is classified and re-stored in a system that is established using a data mining technique (S1000). The re-stored three-dimensional volume image is transmitted through the data transmitting unit 500 to a hospital capable of diagnosing the three-dimensional volume image (S1100). The data transmitting unit 500 first transmits the abnormal three-dimensional volume image that is determined through the pre-diagnosis, and then transmits the normal three-dimensional volume image after completing the transmission of the abnormal three-dimensional volume image or when the diagnosing hospital requests the normal three-dimensional volume image.

Figure 2:
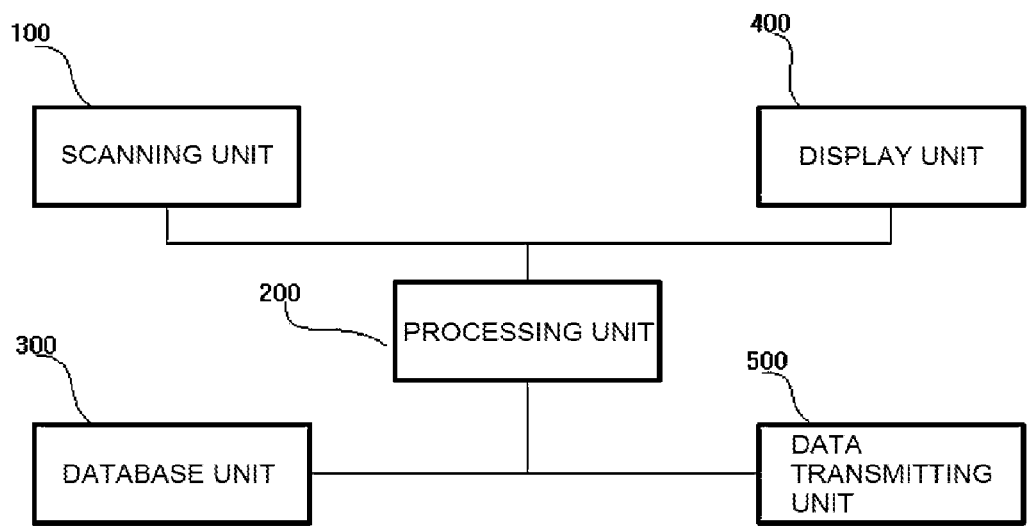
FIG. 2 is a block diagram showing a three-dimensional remote ultrasound diagnostic apparatus according to the present invention.

FIG. 2 is a block diagram showing a three-dimensional remote ultrasound diagnostic apparatus according to the present invention. As shown in FIG. 2, the apparatus includes a scanning unit 100 configured to generate two-dimensional volume images of an inside of a human body using an ultrasonic signal, a processing unit 200 configured to combine the two-dimensional volume images acquired through the scanning unit 100 to generate a three-dimensional volume image and compress and pre-diagnose the three-dimensional volume image in units of a specific part or organ, a database unit 300 configured to store the compressed three-dimensional volume image, a display unit 400 configured to display the three-dimensional data generated through the processing unit 200, and a data transmitting unit 500 configured to transmit the three-dimensional volume image compressed by the processing unit to a diagnosing hospital through a wired/wireless communication, a CD, or a PACS system.

The scanning unit 100 includes a probe that scans an organ inside a human body using an ultrasonic signal to generate a volume image, and the probe includes at least one of a three-axis acceleration sensor, a three-point spatial position sensor, and a gyro sensor to determine a tremor of a hand holding the probe.

The processing unit 200 performs lossless compression on the three-dimensional volume image when a communication rate of the data transmitting unit 500 is equal to or greater than 1 Mbps and performs lossy compression on the three-dimensional volume image when the communication rate is less than 1 Mbps. The communication rate is measured using one or more of a ping rate, a degree of packet loss, and a data transfer rate.

The processing unit 200 determines whether the three-dimensional volume image has an area of interest, and performs lossless compression on the area of interest when the three-dimensional volume image has the area of interest and performs lossy compression on an area of no interest. In a method of extracting the area of interest, the three-dimensional volume image is divided into an area of interest and an area of no interest according to similarity of feature values such as brightness, color, texture, and movement, using an image segmentation technique. The lossless compression is performed on the area of interest, and the lossy compression is performed on the area of no interest. The area of interest may be determined by using a watershed algorithm which is an example of an image segmentation technique or analyzing a change in the gradient of the volume image.

For the lossless compression, one or more of ZIP and RAR are used. Alternatively, another lossless compression scheme may be used to compress images. For the lossy compression, one or more of a wavelet algorithm and a movement compensation algorithm are used. Alternatively, another lossy compression scheme may be used.

The processing unit 200 classifies and stores the three-dimensional volume image in the database unit 300 using a data mining device. The data mining device classifies and stores the three-dimensional volume image according to the attribute information of the patients, establishes the classified and stored three-dimensional volume image as an image group, generates a standard three-dimensional volume image by applying a statistical technique to the patient data that is accumulated in the established image group, and utilizes the generated standard three-dimensional volume image to the pre-diagnosis. The attributes of patients may include race, blood type, height, weight, disease name, and the like.

The processing unit 200 performs the pre-diagnosis in order to efficiently transmit the compressed and stored three-dimensional volume image to a hospital capable of providing a diagnosis. The pre-diagnosis is performed by comparing sizes between the compressed and stored three-dimensional volume image and a normal standard three-dimensional volume image stored in the database unit 300, and determining the compressed and stored three-dimensional volume image as an abnormal three-dimensional volume image when the size of the compressed and stored three-dimensional volume image is greater and determining the compressed and stored three-dimensional volume image as a normal three-dimensional volume image when the size is equal to that of the normal standard three-dimensional volume image. With a statistical similarity verification algorithm, the pre-diagnosis is performed by determining the compressed and stored three-dimensional volume image as the abnormal three-dimensional volume image when a similarity between the three-dimensional volume image and an abnormal standard three-dimensional volume image stored in the database unit 300 is high and determining the compressed and stored three-dimensional volume image as the normal three-dimensional volume image when the similarity is low.

The determined three-dimensional volume image is classified and re-stored in an established image group using a data mining technique. The re-stored three-dimensional volume image is transmitted through the data transmitting unit 500 to a hospital capable of diagnosing the three-dimensional volume image. The data transmitting unit 500 first transmits the abnormal three-dimensional volume image that is determined through the pre-diagnosis, and then transmits the normal three-dimensional volume image after completing the transmission of the abnormal three-dimensional volume image or when the diagnosing hospital requests the normal three-dimensional volume image.

Figure 3:
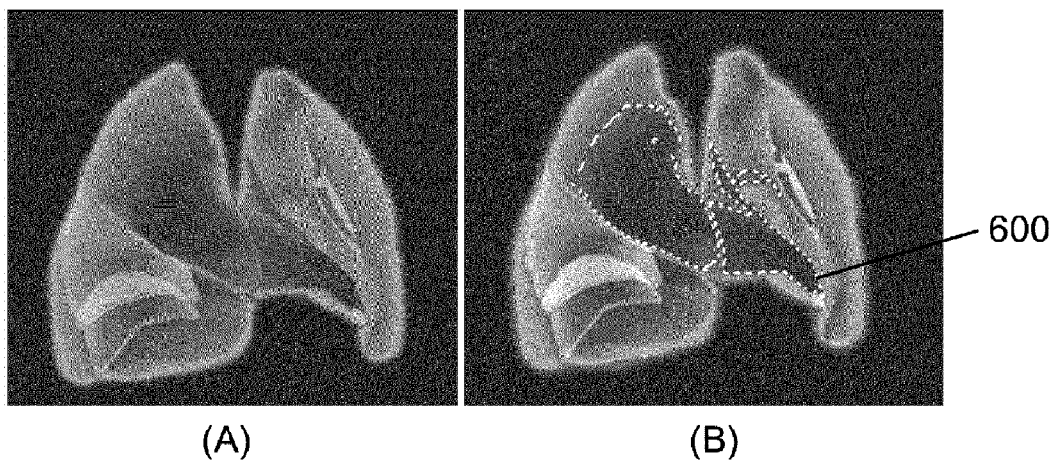
FIG. 3 shows an image of an area of interest according to the present invention.

FIG. 3 shows an image of an area of interest according to the present invention. As shown in FIG. 3, FIG. 3A shows the three-dimensional volume image, and the FIG. 3B shows an area of interest of the three-dimensional volume image. In a method of extracting the area of interest, the area of interest is designated in the three-dimensional volume image by analyzing a change in the gradient of the volume image and using a watershed algorithm to determine features. Alternatively, the area of interest is designated according to similarity of feature values such as brightness, color, texture, and movement of the volume image.

Figure 4:
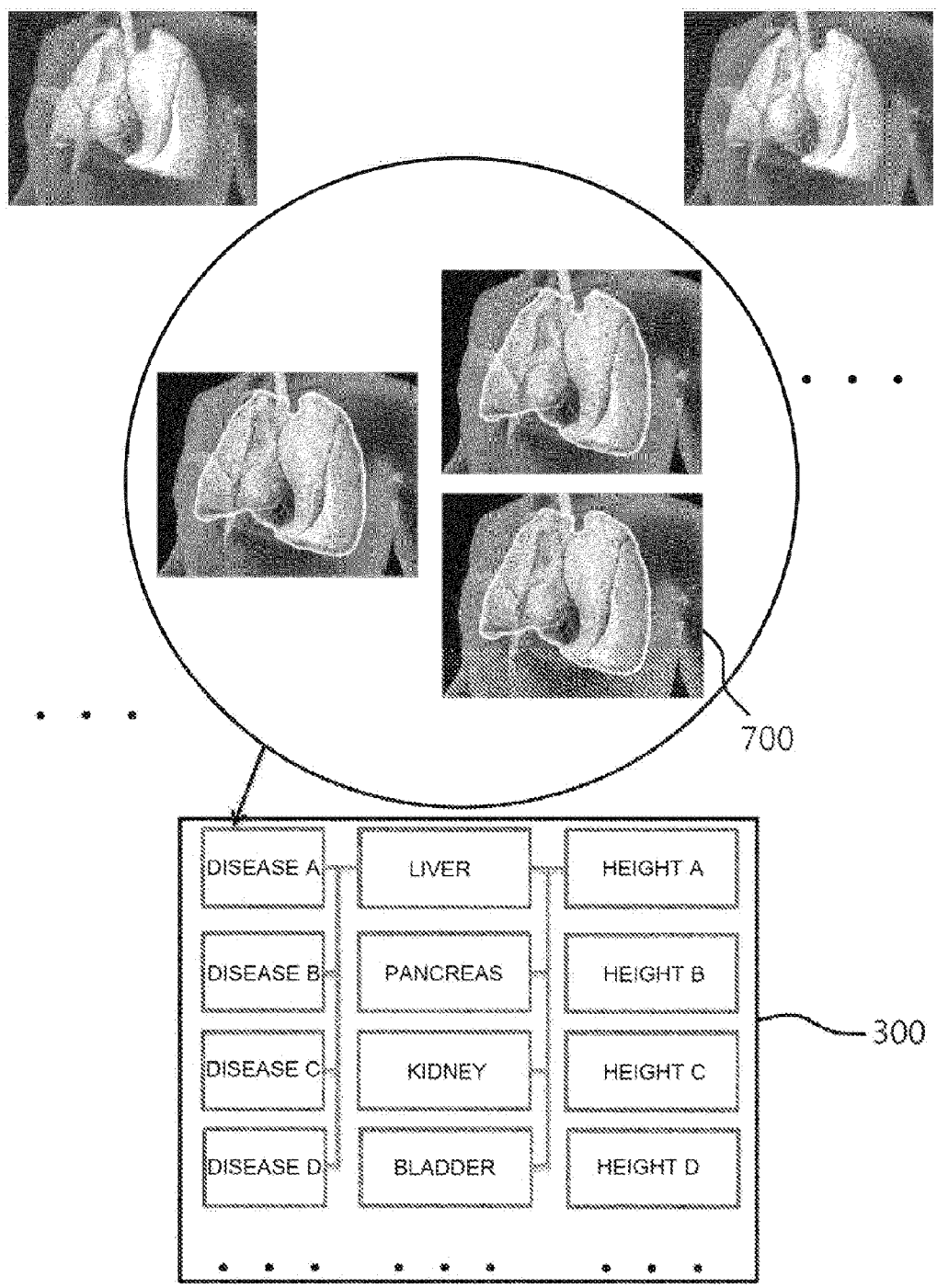
FIG. 4 is a classification diagram of a three-dimensional volume image obtained through data mining according to the present invention.

FIG. 4 is a classification diagram of a three-dimensional volume image obtained using data mining according to the present invention. As shown in FIG. 4, three-dimensional volume images obtained by scanning organs of a human body are classified according to race, blood type, height, weight, disease name, and the like, using a data mining technique and then stored in a database unit 300.

While the invention has been shown and described with reference to certain exemplary embodiments thereof, it will be understood by those skilled in the art that various changes in form and details may be made therein without departing from the spirit and scope of the invention as defined by the appended claims.

The invention claimed is:

1. A method of compressing and pre-diagnosing an image in a three-dimensional remote ultrasound diagnostic apparatus, the method comprising:
   a first step of combining two-dimensional images scanned by a scanning unit and generating a three-dimensional volume image, by a processing unit;
   a second step of selecting a compression scheme for the three-dimensional volume image and compressing the three-dimensional volume image using the selected compression scheme;
   a third step of storing the compressed three-dimensional volume image in a database unit;
   a fourth step of pre-diagnosing an abnormal three-dimensional volume image from among stored three-dimensional volume images; and
   a fifth step of transmitting the abnormal three-dimensional volume image to a hospital capable of providing a diagnosis, by a data transmitting unit.

2. The method of claim 1, wherein the selecting of the compression scheme in the second step is performed by selecting lossless compression of the three-dimensional volume image when a communication rate of the data transmitting unit is equal to or greater than 1 Mbps or by selecting losslessly compression of an area of interest when the three-dimensional volume image has the area of interest.

3. The method of claim 2, wherein the lossless compression uses one or more of ZIP and RAR.

4. The method of claim 2, wherein one or more of the area of interest and the area of no interest are extracted from the three-dimensional volume image using an image segmentation technique.

5. The method of claim 1, wherein the selecting of the compression scheme in the second step is performed by selecting lossy compression of the three-dimensional volume image when a communication rate of the data transmitting unit is less than 1 Mbps or by selecting lossy compression of an area of no interest when the three-dimensional volume image has the area of no interest.

6. The method of claim 5, wherein the lossy compression uses one or more of a wavelet algorithm and a movement compensation algorithm.

7. The method of claim 1, wherein the storing of the three-dimensional volume image in the third step uses data mining.

8. The method of claim 7, wherein the data mining comprises:
classifying and storing the three-dimensional volume image according to attribute information of patients;
establishing the classified and stored three-dimensional volume image as an image group; and
generating a standard three-dimensional volume image by applying a statistical technique to patient data that is accumulated in the established image group, and utilizing the generated standard three-dimensional volume image to provide the pre-diagnosis.

9. The method of claim 8, wherein the attribute information of patients includes one or more of race, blood type, height, and weight.

10. The method of claim 1, wherein the pre-diagnosing is performed by comparing sizes between the compressed and stored three-dimensional volume image and a normal standard three-dimensional volume image stored in the database unit and determining the three-dimensional volume image to be an abnormal three-dimensional volume image when a size of the compressed and stored three-dimensional volume image is greater or by using a statistical similarity verification algorithm to determine the three-dimensional volume image to be the abnormal three-dimensional volume image when a similarity between the three-dimensional volume image and the abnormal three-dimensional volume image stored in the database unit is high.

11. A three-dimensional remote ultrasound diagnostic apparatus that compresses and pre-diagnoses an image, the apparatus comprising:
a scanning unit configured to generate two-dimensional volume images of an inside of a human body using an ultrasonic signal;
a processing unit configured to combine the two-dimensional volume images acquired through the scanning unit to generate a three-dimensional volume image and then compress and pre-diagnose the three-dimensional volume image in units of a specific part or organ; and
a database unit configured to store the compressed three-dimensional volume image.

12. The apparatus of claim 11, further comprising:
a display unit configured to display the three-dimensional data generated through the processing unit; and
a data transmitting unit configured to transmit the three-dimensional volume image compressed by the processing unit to a hospital for diagnosis through one or more of a wired/wireless communication, a CD, and a PACS system.

13. The apparatus of claim 11, wherein the scanning unit comprises a probe, and the probe comprises one or more of a three-axis acceleration sensor, a three-point spatial position sensor, and a gyro sensor.

14. The apparatus of claim 11, wherein the processing unit losslessly compresses the three-dimensional volume image when a communication rate of the data transmitting unit is equal to or greater than 1 Mbps, or losslessly compresses an area of interest when the three-dimensional volume image has the area of interest.

15. The apparatus of claim 14, wherein the lossless compression uses one or more of ZIP and RAR.

16. The apparatus of claim 14, wherein one or more of the area of interest and the area of no interest are extracted from the three-dimensional volume image using an image segmentation technique.

17. The apparatus of claim 11, wherein the processing unit lossily compresses the three-dimensional volume image when a communication rate of the data transmitting unit is less than 1 Mbps, or lossily compresses an area of no interest when the three-dimensional volume image has the area of no interest.

18. The apparatus of claim 17, wherein the lossy compression uses one or more of a wavelet algorithm and a movement compensation algorithm.

19. The apparatus of claim 11, wherein the database unit stores the three-dimensional volume image using a data mining device.

20. The apparatus of claim 19, wherein the data mining device classifies and stores the three-dimensional volume image according to attribute information of patients, establishes the classified and stored three-dimensional volume image as an image group, and generates a standard three-dimensional volume image by applying a statistical technique to patient data that is accumulated in the established image group.

21. The apparatus of claim 20, wherein the attribute information of patients includes one or more of race, blood type, height, and weight.

22. The apparatus of claim 11, wherein the processing unit compares sizes between the compressed and stored three-dimensional volume image and a normal standard three-dimensional volume image stored in the database unit to pre-diagnose the three-dimensional volume image to be an abnormal three-dimensional volume image when a size of the compressed and stored three-dimensional volume image is greater, or uses a statistical similarity verification algorithm to pre-diagnose the three-dimensional volume image to be the abnormal three-dimensional volume image when a similarity between the three-dimensional volume image and the abnormal three-dimensional volume image stored in the database unit is high.

* * * * *